(12) United States Patent
Gambogi et al.

(10) Patent No.: US 6,180,089 B1
(45) Date of Patent: Jan. 30, 2001

(54) DUAL COMPONENT DENTINAL DESENSITIZING DENTIFRICE

(75) Inventors: Robert J. Gambogi, Belle Mead; Steven W. Fisher, Middlesex; Edward A. Tavss, Kendall Park; Marilou T. Joziak, South River; James G. Masters, Ringoes, all of NJ (US)

(73) Assignee: Colgate-Palmolive Company, New York, NY (US)

(*) Notice: Under 35 U.S.C. 154(b), the term of this patent shall be extended for 0 days.

(21) Appl. No.: 09/234,829

(22) Filed: Jan. 21, 1999

(51) Int. Cl.[7] .................. A61K 7/16; A61K 7/18
(52) U.S. Cl. ........................... 424/52; 424/49
(58) Field of Search ..................... 424/49–58

(56) References Cited

U.S. PATENT DOCUMENTS

| | | | |
|---|---|---|---|
| 3,863,006 | * 1/1975 | Hodosh | 424/49 |
| 4,487,757 | * 12/1984 | Kizpeoplou | 424/49 |
| 4,687,663 | * 8/1987 | Schaeffer | 424/49 |
| 5,085,853 | * 2/1992 | Williams et al. | 424/49 |
| 5,256,402 | * 10/1993 | Prencipe et al. | 424/53 |
| 5,275,805 | * 1/1994 | Nabi et al. | 424/54 |
| 5,565,190 | * 10/1996 | Santalucia et al. | 424/53 |
| 5,599,525 | * 2/1997 | Hsu et al. | 424/49 |
| 5,599,527 | * 2/1997 | Hsu et al. | 424/52 |
| 5,614,174 | * 3/1997 | Hsu et al. | 424/49 |
| 5,683,680 | * 11/1997 | Santalucia et al. | 424/53 |
| 5,690,913 | * 11/1997 | Hsu et al. | 424/53 |
| 5,756,073 | * 5/1998 | Miller et al. | 424/49 |
| 5,766,574 | * 6/1998 | Christina-Beck et al. | 424/49 |
| 5,780,015 | * 7/1998 | Fisher et al. | 424/49 |
| 5,814,303 | * 9/1998 | Williams et al. | 424/49 |
| 5,846,570 | * 12/1998 | Barrow et al. | 424/57 |
| 5,855,875 | * 1/1999 | Williams et al. | 424/49 |
| 5,876,701 | * 3/1999 | Wong et al. | 424/49 |
| 5,902,568 | * 5/1999 | Ryles et al. | 424/49 |

* cited by examiner

*Primary Examiner*—Shep K. Rose
(74) *Attorney, Agent, or Firm*—Paul Shapiro

(57) ABSTRACT

A two component dental composition is disclosed which eliminates or substantially reduces the discomfort and pain associated with dentinal hypersensitivity which composition comprises a first dentifrice component having an alkaline pH, a second dentifrice component having an acid pH and at least one of the components containing a potassium ion releasable compound, the first and second components being maintained separate from each other until dispensed and combined for application to teeth requiring relief from dentine hypersensitivity, whereby heightened desensitization is experienced by the user.

19 Claims, 1 Drawing Sheet

DUAL COMPONENT DENTINAL DESENSITIZING DENTIFRICE

BACKGROUND OF TIME INVENTION

1. Field of the Invention

The present invention relates to a desensitizing dentifrice composition which eliminates or reduces the discomfort and pain associated with dentinal hypersensitivity and more particularly to a two-component desensitizing dental composition containing potassium salt desensitizing agents.

2. The Prior Art

Dentinal hypersensitivity is defined as acute, localized tooth pain in response to physical stimulation of the dentine surface as by thermal (hot or cold) osmotic, tactile combination of thermal, osmotic and tactile stimulation of the exposed dentin.

Exposure of the dentine, which is generally due to recession of the gums, or loss of enamel, frequently leads to hypersensitivity. The art has determined that dentine tubules open to the surface have a high correlation with dentine hypersensitivity, Abs, J. Clin. Periodontal. 14,280–4 (1987). Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients.

It is known to the art that potassium salts are effective in the treatment of dentinal hypersensitivity. For example, U.S. Pat. No. 3,863,006 discloses that toothpastes containing potassium salts such as potassium nitrate desensitize the teeth after tooth brushing for several weeks. It is believed by those skilled in the art that an elevation in the extracellular potassium concentration in the vicinity of pulpal nerves underlying sensitive dentin is responsible for the therapeutic desensitizing effect of topically applied oral products which contain potassium nitrate. Due to passive diffusion of potassium ion into and out of the open dentine tubules, repeated application of the active ingredient is necessary to build up the necessary concentration in the vicinity of the pulpal nerves.

It is believed that the improved pain relief is obtained from the use of potassium salts in combination with gradual mineralization on the dentin surface which can either totally or partially occlude dentin tubules. Total occlusion will dramatically reduce fluid flow within the tubules which stimulates pain. Partial occlusion of the dentin tubules is believed to increase delivery of potassium ion inside the tooth because the inward diffusive flux is less dependent upon tubule radius than outward fluid flow (due to positive pulpal pressures) (See D H Pashley and W G Mathews, Archs. Oral Biol. (1993) 38, 577–582). Therefore, this enhanced delivery of potassium should enhance relief.

Although potassium salts such as potassium nitrate are highly effective in the treatment of dentine hypersensitivity, the art continuously seeks means to improve the efficacy of such treatment.

SUMMARY OF THE INVENTION

The present invention is based upon the discovery that when a dual component dentifrice comprised of separately housed dentifrice components of acidic and alkaline pH at least one component containing a potassium salt are combined before use, the combined composition exhibits unexpected improved effectiveness when applied to the teeth in obturating dentinal tubules with concomitant desensitization of teeth as compared to single component compositions of neutral pH.

In accordance with the present invention there is provided a method for the treatment of dentinal hypersensitivity using a multicomponent dentifrice comprised of two separately housed, semi-solid aqueous components; the first component containing a fluoride salt as the source of fluoride ions, in an orally acceptable vehicle having an alkaline pH of at least about 8.0 and preferably about 9.0 to about 10.5 and, the second component containing an acid to provide an acid pH from about 1.0 to about 6.0 preferably about 1.0 to about 3.0 in an orally acceptable vehicle, at least one component containing a fluoride ion releasing compound such as a water soluble, potassium ion releasable compound whereby upon mixing and combination of the components, a mixture having a pH of from about 6.5 to about 9.0, preferably about 7.0 to about 8.5, is formed whereby upon repeated application of the mixture to the teeth increased relief from dentinal hypersensitivity is experienced by the user.

IN THE DRAWINGS

DESCRIPTION OF THE PREFERRED EMBODIMENTS

Figure 1:
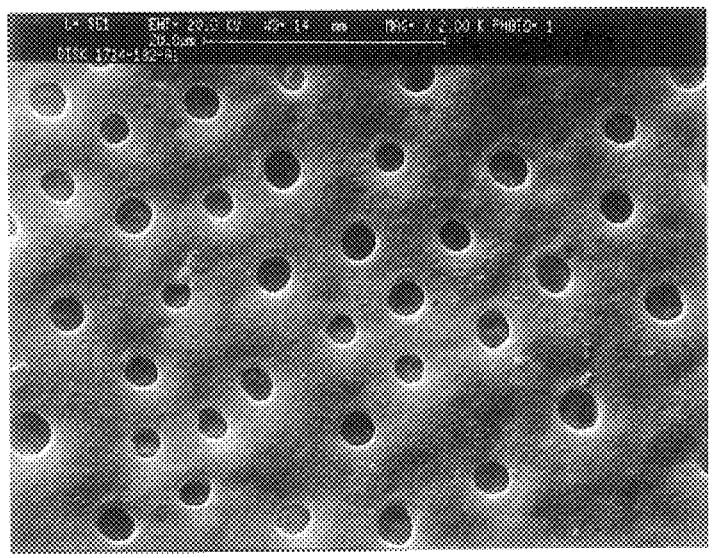
FIG. 1 is a scanning electron photomicrograph (SEM) (2,000× magnification) of a dentin disk surface treated with phosphate buffer solution.

In use, the components of the two component dentifrice of the present invention comprise a first alkaline dentifrice component, and a second acidic dentifrice component. The two components are preferably combined in approximately equal weight proportions, so that about one-half of the concentration of any particular ingredient within either component will be present when the components are combined and applied to the teeth, as by brushing. Both components are preferably formulated to have similar physical characteristics, so that the two components may be simultaneously delivered in the desired predetermined amounts by extrusion when separately housed in a multicompartmented tube or pump device.

To prepare the alkaline dentifrice component of the present invention, an alkaline agent is generally incorporated in the dentifrice component which normally includes a vehicle which contains water, humectant, surfactant and an abrasive. The pH of such dentifrice is in the alkaline range of about 8.0 to 11.0 and preferably about 9.0 to about 10.5. The acidic dentifrice component is prepared using a similar vehicle, the pH of such dentifrice being in the acid range of about 1.0 to about 6.0 and preferably about 1.0 to about 3.0.

The humectant used in the preparation of the dentifrice components is generally a mixture of humectants, such as glycerol, sorbitol and a polyethylene glycol of molecular weight in the range of 200 to 1000, but other mixtures of humectants and single humectants may also be employed.

The humectant content is in the range about of 10% to about 80% by weight and preferably about 20 to about 50% by weight of the dentifrice component. The water content is in the range of about 10 to about 40% by weight and preferably about 20 to about 30% by weight.

Thickeners include organic and inorganic thickeners. Inorganic thickeners which may be included in the dentifrice components include amorphous silicas such as Zeodent 165 available from Huber Corporation, and Sylox 15 from W. R. Grace.

Organic thickeners of natural and synthetic gums and colloids may also be used to prepare the dentifrice components of the present invention. Examples of such thickeners are carrageenan (Irish moss), xanthan gum, sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The inorganic thickener may be incorporated in the dentifrice components of the present invention at a concentration of about 0.5 to about 5% by weight and preferably about 1 to about 3% by weight. The organic thickener may be incorporated in the compositions of the present invention at a concentration of about 0.1 to about 3% by weight and preferably about 0.4 to about 1.5% by weight.

Surface active agents may be incorporated in the dentifrices to provide foaming properties. The surface-active material is preferably anionic or nonionic in nature. Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate.

The surface active agent is generally present in the dentifrice component compositions of the present invention at a concentration of about 0.5 to about 10.0% by weight and preferably about 1.0 to about 5.0% by weight.

Abrasives may be incorporated in the dentifrice components of the present invention and preferred abrasives are siliceous materials, such as silica. A preferred silica is a precipitated amorphous hydrated silica, such as Sorbosil AC-35, marketed by Crosfield Chemicals, or Zeodent 115 from Huber Company but other abrasives may also be employed, including hydroxyapatite, sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, sodium bicarbonate, alumina trihydrate, aluminum silicate, calcined alumina and bentonite.

The concentration of abrasive in the dentifrice component compositions of the present invention will normally be in the range of 2 to about 40% by weight and preferably 5 to 25% by weight.

Alkaline agents such as alkali metal compounds including sodium hydroxide, potassium hydroxide, sodium bicarbonate, sodium carbonate are incorporated in the alkaline dentifrice component of the present invention in amounts in the range of about 0.5 to 15% by weight, preferably about 1.0 to about 8% by weight and most preferably at about 1.0 to about 5.0% by weight of the component. Mixtures of the above alkali metal compounds may also be used. Sodium hydroxide is the preferred alkaline agent.

The acidic dentifrice component of the dentifrice composition of the present invention, which is maintained physically separate from the alkaline dentifrice component until mixing before use, contains an acid or mixture of acids, to acidulate the alkaline dentifrice component, so that when the two components are combined prior to use, the combined dentifrice is at a pH in the range of about 6.5 to about 9.0, preferably about 7.0 to about 8.5.

Acidic compounds which can be present in the acidic component include both mineral and organic acids, such as, sulfuric acid, hydrochloric acid, malic acid, alginic acid, citric acid, succinic acid, lactic acid, tartaric acid, potassium bitartrate, acid sodium citrate, phosphoric acid, and sodium acid phosphate. Acid phosphates are preferred, including phosphoric acid, or salts of phosphoric acid containing the $PO_4$ ion, as such acids or acid salts thereof, such as sodium phosphate monobasic, not only provide the necessary acidity, but also provide phosphate ions, to inhibit any tooth enamel demineralization which may occur with the application of the two component acidulated dentifrice to the teeth. Further, the combination of an acid such a phosphoric acid and an acid salt, such as sodium phosphate monobasic, provides enhanced buffering to achieve the desired pH upon the mixing of the dentifrice components. The preferred acid, phosphoric acid is commercially available as a liquid at 85% concentration. The acid is added to the dentifrice component in an amount to maintain the pH of the dentifrice at a pH of about 1.0 to about 6.0 and preferably about 1.0 to about 3.0.

Calcium ion salt sources such as calcium chloride, calcium acetate and dicalcium phosphate dihydrate may be added to the non-fluoridated dentifrice composition to further enhance the mineralizing potential of this composition upon combination with the fluoridated dentifrice component. The concentration of the calcium salts is in the range of about 0.5 to 20 percent depending upon the solubility of the salt and the interaction with other dentifrice ingredients.

The source of desensitizing potassium ion is generally a water soluble potassium salt including potassium nitrate, potassium citrate, potassium chloride, potassium bicarbonate and potassium oxalate with potassium nitrate being preferred. The potassium salt is generally incorporated in one or more of the dentifrice components at a concentration of about 0.5 to about 20% by weight and preferably about 3 to about 15% by weight.

Fluoride providing salts having anticaries efficacy may also be incorporated in the dentifrice of the present invention and are characterized by their ability to release fluoride ions in water. It is preferable to employ a water soluble fluoride salt providing about 10–2,000 ppm of fluoride ion, and preferably about 1000–1500 ppm of fluoride ion. Among these materials are water soluble inorganic metal salts, for example, sodium fluoride, potassium fluoride, sodium monofluorophosphate, stannous fluoride and sodium fluorosilicate. Sodium fluoride, sodium monoflurophosphate and stannous fluoride are preferred fluoride providing salts.

Pyrophosphate salts having anticalculus efficacy useful in the practice of the present invention include water soluble salts such as dialkali or tetraalkali metal pyrophosphate salts such as $Na_4P_2O_7$ (TSPP), $K_4P_2O_7$, $Na_2K_2P_2O_7$, $Na_2H_2P_2O_7$ and $K_2H_2P_2O_7$. Polyphosphate salts include the water soluble alkali metal tripolyphosphates such as sodium tripolyphosphate and potassium tripolyphosphate.

The pyrophosphate salts are incorporated in the dentifrice composition of the present invention at a concentration of about 0.5 to about 2.0% by weight, and preferably about 1.5 to about 2% by weight and the polyphosphate salts are incorporated in the dentifrice composition of the present invention at a concentration of about 1.0 to about 7.0% by weight.

Colorants such as pigments and dyes may be used in the practice of the present invention. Pigments include nontoxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5-1000 microns, preferably 250–500 microns, and are present at a concentration of 0.5 to 3% by weight.

Dyes used in the practice of the present invention are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium slat of 4-{[4-(N-ethyl-p-sulffobenzylamino)-phenyl]-(4-hydroxy-2-sulfoniumphenyl)-mewthylene}-[1-N-ethyl-N-p-sulfobenzyl)-Δ-3,5-cyclohexadienimine], FD&C Blue No. 1 (disodium salt of dibenzyldiethyldiaminotriphenylcarbinol trisulfonic acid of indigotin) and mixtures thereof in various proportions. The concentration of the dye for the most effective result in the present invention is present in the dentifrice composition in an amount from about 0.0005 percent to about 2 percent of the total weight.

A striped dentifrice product may be obtained using the dual component dentifrice of the present invention, wherein colorants of contrasting colors are incorporated in each of the dentifrice components to be dispensed; the colorants being pharmacologically and physiologically non-toxic when used in the suggested amounts. Colorants used in the practice of the present invention include both the pigments and dyes discussed above.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon lemon, and orange, and methyl salicylate. Suitable sweetening agents include sucrose, lactose, maltose, sorbitol, xylitol, sodium cyclamate, perillatine, and sodium saccharin. Suitably, flavor and sweetening agents may together comprise from 0.01% to 5% or more of the preparations.

Antibacterial agents are non-cationic antibacterial agents based on phenolic and bisphenolic compounds, halogenated diphenyl ethers such as Triclosan, benzoate esters and carbanilides as well as cationic antibacterial agents such as chlorhexidine digluconate. Such antibacterial agents can be present in quantities of from about 0.03 to about 1% by weight of the particular component.

When noncationic antibacterial agents or antibacterial agents are included in any of the dentifrice components, there is also preferably included from about 0.05 to about 5% of an enhancing agent which enhances the delivery and retention of the agents to, and retention thereof on oral surfaces. Enhancing agents useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g. AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from 0.05 to about 3% by weight.

To prepare either of the dentifrice components of the present invention, generally the humectants e.g. glycerin, propylene glycol, polyethylene glycol ingredients, are dispersed with any organic thickeners, sweetener, pigments such as titanium dioxide and any polyphosphates included as anti-calculus ingredients. Water is then added into this dispersion along with any antibacterial agent such as Triclosan, any antibacterial enhancing agent such as Gantrez and any anticalculus additional agents. In the first component (or both) a fluoride ion source and an alkaline agent such as sodium hydroxide is added. In the second component an ingredient to lower the pH to an acid level is added such as phosphoric acid. These ingredients are mixed until a homogenous phase is obtained for each component. Thereafter inorganic thickener, silica abrasive, flavor and surfactant ingredients are added and the ingredients mixed at high speed under vacuum of from about 20 to 100 mm of Hg. The resultant product is in the case of each component is a homogeneous, semi-solid, extrudible paste product.

The multicomponent dentifrice composition of the present invention is packaged in a suitable dispensing container in which the components are maintained physically separated and from which the separated components may be dispensed synchronously as a combined ribbon for application to a toothbrush. Such containers are known in the art. An example of such a container is a two compartment dispensing container, such as a pump or a tube, having collapsible sidewalls, as disclosed in U.S. Pat. Nos. 4,487,757 and 4,687,663; wherein, the tube body is formed from a collapsible plastic web such as polyethylene or polypropylene and is provided with a partition within the container body defining separate compartments in which the physically separated components are stored and from which they are dispensed through a suitable dispensing outlet.

The following example is further illustrative of the present invention, but it is understood that the invention is not limited thereto. All amounts and proportions referred to herein and in the appended claims are by weight, unless otherwise stated.

EXAMPLE

A two component (Component A and B) desensitizing dentifrice of the present invention was prepared, designated Dentifrice I, Component A having an alkaline pH and a Component B having an acid pH. The ingredients and pH of Components A and B are listed in Table I, below.

TABLE I

| | Dentifrice I Weight % | |
|---|---|---|
| Component Ingredients | A Alkaline paste | B Acidic paste |
| Deionized Water | 28.714 | 32.316 |
| Sodium Fluoride | 0.486 | — |
| Potassium Nitrate | 10.000 | — |
| H3PO4 (85%) | — | 2.880 |
| Glycerin | 25.000 | 33.704 |
| Polyethylene glycol 600 | 3.000 | — |
| Xanthan | 0.600 | 0.800 |
| Carboxymethyl cellulose | 0.400 | 0.000 |
| Sodium saccharin | 0.400 | 0.400 |
| Titanium Dioxide | 2.000 | 0.000 |
| Pluronic F-127 | 1.000 | 2.000 |
| Sodium Hydroxide (50%) | 3.000 | — |
| FD&C Blue #1 (1% solution) | — | 0.300 |
| Zeodent 115 | 15.000 | 22.000 |
| Zeodent 165 | 3.000 | 3.000 |
| Sodium Bicarbonate | 5.000 | — |
| Sodium lauryl sulfate | 1.500 | 1.500 |
| Flavor | 0.900 | 1.100 |
| pH (as is) | 9.9 | 1.3 |

In the preparation of Dentifrice I, the glycerin, polyethylene glycol and organic thickeners were dispersed in a conventional mixer until the mixture became a slurry, which was smooth in appearance. Color and sweetener were dispersed in this slurry before the addition of water. In the preparation of Component A, potassium nitrate was then dispersed in this slurry. In the preparation of Component B, phosphoric acid was then dispensed in the gel phase. This mixture was mixed for 20 to 30 minutes producing a homogeneous gel phase. The mixture was added to a vacuum mixer and cooled below 105° F. Zeodent 115, Zeodent 165 and sodium bicarbonate were then added and mixed for 10 to 30 minutes at high speed under a vacuum of about 50 mm Hg, providing a homogenous mixture. The sodium lauryl sulfate and flavor were then added to the individual dentifrice components which was followed by mixing another 5–15 minutes under vacuum of 50 mm Hg to prepare the resultant component product.

The desensitizing efficacy of the two component composition described above was evaluated using 4.25 mm×4.25 mm square dentin disks of 750 μm thickness cut from extracted human molars. The disks were prepared for treatment by etching with 6% citric acid for 2 minutes to remove any surface smear.

The rate of flow of a phosphate buffer solution (0.2 mm phosphate, 0.2 mm $CaCl_2$ and 0.1M NaCl at pH=7) through the disks under 70mm water pressure were measured to determine baseline flow rates, the disks being divided into groups of three each such that the average flow rates between the groups were similar.

The dentin disks were then treated by brushing for a 45 second period with the combined components of Dentifrice I at a 1:1 volume ratio. The pH of the combined components was 7.40 when diluted 1:1 with deionized water.

For purposes of comparison the procedure of the Example was repeated with another group of similarly prepared disks using a single component commercially available desensitizing toothpaste designated Toothpaste "C" contained both 0.76% by weight NaMFP and 5% by weight $KNO_3$. As a control, the procedure of the Example was repeated using the phosphate buffer solution as the treatment which treatment was designated "Control".

The treated disks were immersed in 10–25 ml of tap water and agitated with the end of a toothbrush to remove dentifrice from the disk surface. The disks were put into the phosphate buffer solution between brushings. The disks were treated twelve (12) times each over a four day period.

Artificial saliva (pH=7) having the following composition:

| | |
|---|---|
| Phosphate ion | 0.2 mM (millimole) |
| $CaCl_2$ | 6.2 mM |
| NaCl | 150.0 mM | was milligrams of artificial saliva per second at this pressure which flow rates are recorded in Table II below.

TABLE II

| Treatment | Average Flow (mg/s)* |
|---|---|
| 1. Dentifrice I | 0.443 |
| 2. Toothpaste C | 1.02 |
| 3. Control | 1.53 |

*Average of 3 replicates

The flow rates of artificial saliva solution through the dentin disks recorded in Table II indicate that Dentifrice I has a pronounced effect on reducing flow relative to the comparative commercial dentifrice, Dentifrice C, and the phosphate buffer solution Control. The reductions in flow are believed to be due to occlusion of the dentinal tubules. The occlusive state produced by the Dentifrice I treatment is considered by the art to be predictive of clinical dentinal hypersensitivity reduction (M. Brannstrom and A. Astrom, J. Dent. Res. (1964) 43, 619. 625.

The treated disks which were subjected to the flow measurements were subjected to Electron Spectroscopy for Chemical Analysis (ESCA) and Scanning Electron Microscopy (SEM) analysis. Before these analysis were conducted, the disks were rinsed with deionized water to remove the phosphate buffer solution and dried.

The surface composition of the dentin disks above evaluated using ESCA is recorded in Table III as an average for each group. The percentage of nitrogen on the dentin surface is generally attributed to the amount of exposed collagen material which is an integral part of the dentin structure. A reduced amount of nitrogen is indicative of a surface coating.

TABLE III

| | Atomic Percent | | | | | |
|---|---|---|---|---|---|---|
| Treatment | C | O | N | Ca | P | Si |
| Dentifrice I | 41.91 | 37.03 | 8.02 | 4.87 | 3.70 | 3.80 |
| Dentifrice C | 46.33 | 32.21 | 11.62 | 5.17 | 4.15 | 0.52 |
| Phosphate buffer solution | 60.49 | 22.43 | 15.18 | 0.64 | 0.49 | 0.77 |

These results recorded in Table III indicate that the amount of deposit formed on the surface of the dentin disks treated with the combined components of Dentifrice I is substantially greater than the disks treated with Toothpaste C. The atomic percentages of Si and O in the dentin surfaces treated with Dentifrice I are indicative of high deposits of silica.

Figure 2:
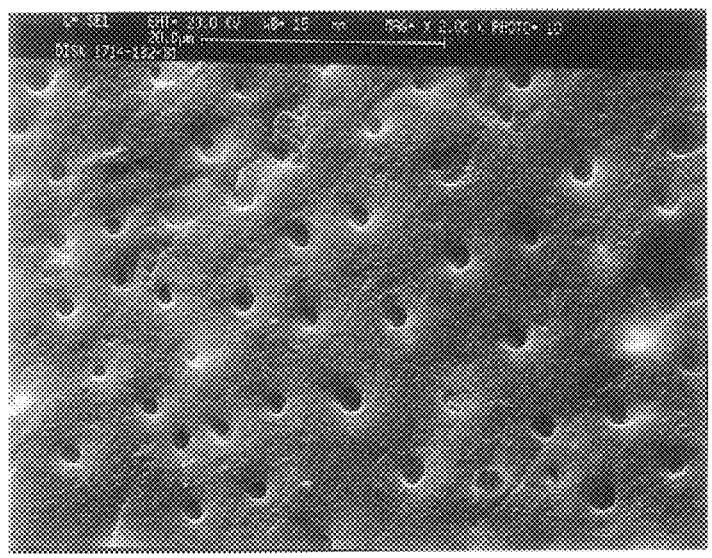
FIG. 2 is a SEM (2,000× magnification) of a dentin disk surface treated in a single component dentifrice containing both NaMFP (0.76% by weight) and potassium nitrate (5% by weight), the pH of the dentifrice being 6.1.
Figure 3:
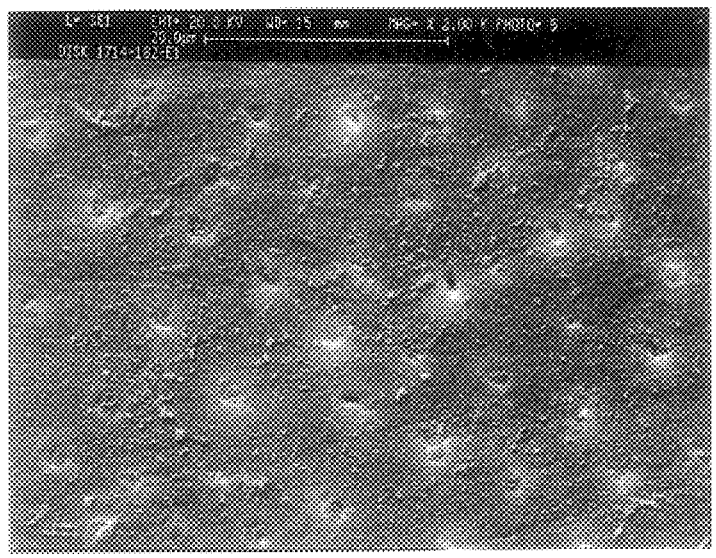
FIG. 3 is a SEM (2,000× magnification) of a dentin disk surface treated with a combined dual component dentifrice containing both NaF (0.243% by weight) and $KNO_3$ (5% by weight), the pH of the NaF dentifrice being 1.3 and the pH of the $KNO_3$ dentifrice being 9.9.

The SEM photomicrographs taken of the dentin surfaces subjected to the treatments of Table III are shown in FIGS. 1–3 respectively. Examination of the photomicrograph of the Dentifrice I treated dentin surface, FIG. 3, indicates that dentinal tubule obturation was substantially complete as compared to treatment with comparative single component Toothpaste C, whereby examination of the photomicrograph of FIG. 2 indicates minimal dentinal tubule obturation using this comparative treatment. The Control treatment of the disks in a phosphate buffer solution as shown in the photomicrograph of FIG. 1 indicated no dentinal tubule obturation.

The flow data, the ESCA data and the SEM data all provide evidence that the unique combination of the acidic and alkaline dentifrice components with either one or both components containing a potassium ion source effects an unexpected substantial improvement in the remediation of dentinal hypersensitivity.

What is claimed is:

1. A two component dental composition packaged in a dual chamber dispensing container which eliminates or substantially reduces the discomfort and pain associated with dentinal hypersensitivity which composition comprises a first dentifrice component separately housed from a second component, the first component having a pH adjusted to an alkaline value of about 8.0 to about 10.5 with an alkali metal compound, a second dentifrice component having a pH adjusted to an acid value of about 1.0 to about 6.0 with an acidic compound and at least one of the components containing a potassium ion releasable compound as the sole desensitizing compound, and a fluoride salt other than stannous fluoride, the first and second components being maintained separate from each other until dispensed and combined for application to teeth requiring relief from dentine hypersensitivity, whereby heightened desensitization is experienced by the user.

2. The composition of claim 1 wherein the potassium ion releasable compound is a water soluble potassium salt.

3. The composition of claim 2 wherein the potassium salt is potassium nitrate.

4. The composition of claim 2 wherein the potassium salt is present in the first dentifrice component.

5. The composition of claim 4 wherein a fluoride salt is present in the first component of the dental composition.

6. The composition of claim 1 wherein the alkaline dentifrice component is an aqueous dentifrice having a pH of about 9 to about 11.

7. The composition of claim 1 wherein the pH of the alkaline dentifrice component is adjusted with sodium hydroxide.

8. The composition of claim 1 wherein a silica abrasive is present in the dentifrice component.

9. The composition of claim 1 wherein the acidic dentifrice component is an aqueous dentifrice having a pH of about 1.0 to about 6.0.

10. The composition of claim 1 wherein the pH of the acidic dentifrice component is adjusted with $H_3PO_4$.

11. A method for eliminating or reducing the discomfort and pain associated with dentinal hypersensitivity which comprises preparing (1) a first dentifrice component having a pH adjusted to an alkaline value of about 8.0 to about 10.5 with an alkali metal compound and (2) a second dentifrice component having a pH adjusted to an acid value of about 1.0 to about 6.0 with an acidic compound, at least one of the components containing a desensitizing potassium ion releasable compound as the sole desensitizing compound, and a fluoride salt other than stannous fluoride separately housing the first and second components, dispensing the first and second components and combining the dispensed components for application to teeth requiring relief from dentine hypersensitivity and thereafter applying the combined components to the teeth whereby heightened desensitization is experienced by the user.

12. The method of claim 11 wherein the potassium compound is a water soluble potassium salt.

13. The method of claim 10 wherein the potassium salt is potassium nitrate.

14. The method of claim 12 wherein the potassium salt is present in the first dentifrice component.

15. The method of claim 14 wherein a fluoride salt is present in the first component of the composition.

16. The method of claim 11 wherein the alkaline dentifrice component is an aqueous dentifrice having a pH of about 9 to about 11.

17. The method of claim 11 wherein the pH of the alkaline dentifrice component is adjusted to an alkaline pH with sodium hydroxide.

18. The method of claim 11 wherein the acidic dentifrice component is an aqueous dentifrice having a pH of about 1.0 to about 6.0.

19. The method of claim 10 wherein the pH of the acidic dentifrice component is adjusted with $H_3PO_4$.

* * * * *